(12) United States Patent
Weitzner et al.

(10) Patent No.: US 7,922,684 B2
(45) Date of Patent: Apr. 12, 2011

(54) ANTI-OBESITY DUAL STENT

(75) Inventors: Barry Weitzner, Acton, MA (US);
Katie Krueger, Merrimack, NH (US);
Claude Clerc, Marlboro, MA (US);
William Bertolino, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1020 days.

(21) Appl. No.: 11/443,402

(22) Filed: May 30, 2006

(65) Prior Publication Data

US 2007/0282452 A1 Dec. 6, 2007

(51) Int. Cl.
*A61M 5/00* (2006.01)
*A61F 2/04* (2006.01)
*A61F 2/06* (2006.01)

(52) U.S. Cl. ..... 604/8; 623/23.65; 623/23.7; 623/23.64; 623/1.15

(58) Field of Classification Search ..... 604/8; 623/23.7, 623/26.5, 26.4, 1.15
See application file for complete search history.

(56) References Cited

U.S. PATENT DOCUMENTS

| | | | |
|---|---|---|---|
| 4,315,509 A | 2/1982 | Smit | |
| 4,582,067 A * | 4/1986 | Silverstein et al. | 600/455 |
| 5,820,584 A * | 10/1998 | Crabb | 604/500 |
| 6,146,389 A | 11/2000 | Geitz | |
| 6,254,642 B1 * | 7/2001 | Taylor | 623/23.64 |
| 6,279,460 B1 * | 8/2001 | Pope | 99/299 |
| 6,499,487 B1 * | 12/2002 | McKenzie et al. | 128/898 |
| 6,576,005 B1 | 6/2003 | Geitz | |
| 6,740,121 B2 | 5/2004 | Geitz | |
| 6,755,869 B2 | 6/2004 | Geitz | |
| 7,211,114 B2 * | 5/2007 | Bessler et al. | 623/23.65 |
| 7,220,237 B2 * | 5/2007 | Gannoe et al. | 604/8 |
| 7,314,489 B2 * | 1/2008 | McKenna et al. | 623/23.65 |
| 7,354,454 B2 * | 4/2008 | Stack et al. | 623/23.65 |
| 2003/0040804 A1 | 2/2003 | Stack et al. | |
| 2003/0120257 A1 * | 6/2003 | Houston et al. | 604/523 |

(Continued)

FOREIGN PATENT DOCUMENTS

EP    0733379    9/1996

(Continued)

OTHER PUBLICATIONS

PCT Notification of Transmittal of the International Search Report and the Written Opinion of the International Searching Authority, or the Declaration for International Application No. PCT/US2007/012266, Nov. 13, 2007 (2 pages).

(Continued)

*Primary Examiner* — Tatyana Zalukaeva
*Assistant Examiner* — Susan Su
(74) *Attorney, Agent, or Firm* — Hoffmann & Baron, LLP

(57) ABSTRACT

The anti-obesity dual stent includes a tubular outer structure within which is located a coaxial tubular inner structure. The outer structure is sized to fit within a duodenum in substantially coaxial relation therewith. The outer and inner structures communicate with the pylorus and papilla of Vater to provide conduits for the chyme and digestive fluid. Alternatively, the anti-obesity dual stent may include a tubular papilla-supplied structure which has a lateral orientation relative to a tubular pylorus-supplied structure. The papilla-supplied and pylorus-supplied structures each are sized to fit longitudinally within the duodenum. The pylorus-supplied and papilla-supplied structures communicate with the pylorus and papilla of Vater to provide conduits for the chyme and digestive fluid.

12 Claims, 3 Drawing Sheets

U.S. PATENT DOCUMENTS

| | | | |
|---|---|---|---|
| 2003/0199989 A1* | 10/2003 | Stack et al. | 623/23.65 |
| 2003/0199990 A1* | 10/2003 | Stack et al. | 623/23.65 |
| 2003/0199991 A1* | 10/2003 | Stack et al. | 623/23.65 |
| 2003/0236483 A1* | 12/2003 | Ren | 604/8 |
| 2004/0006299 A1* | 1/2004 | Barbut | 604/8 |
| 2004/0039452 A1* | 2/2004 | Bessler | 623/23.65 |
| 2004/0107004 A1 | 6/2004 | Levine et al. | |
| 2004/0117031 A1* | 6/2004 | Stack et al. | 623/23.65 |
| 2004/0199262 A1* | 10/2004 | Dua et al. | 623/23.7 |
| 2004/0220682 A1 | 11/2004 | Levine et al. | |
| 2004/0249362 A1 | 12/2004 | Levine et al. | |
| 2005/0043817 A1* | 2/2005 | McKenna et al. | 623/23.65 |
| 2005/0075622 A1* | 4/2005 | Levine et al. | 604/500 |
| 2005/0080395 A1 | 4/2005 | Levine et al. | |
| 2005/0125075 A1 | 6/2005 | Meade et al. | |
| 2006/0106332 A1* | 5/2006 | Knudson et al. | 604/8 |
| 2007/0016306 A1* | 1/2007 | Dua et al. | 623/23.68 |
| 2008/0033574 A1* | 2/2008 | Bessler et al. | 623/23.68 |
| 2008/0228126 A1* | 9/2008 | Bessler | 604/9 |
| 2009/0062717 A1* | 3/2009 | Laufer | 604/8 |

FOREIGN PATENT DOCUMENTS

| | | |
|---|---|---|
| EP | 1508312 | 2/2005 |

OTHER PUBLICATIONS

PCT International Search Report for International Application No. PCT/US2007/012266, Nov. 13, 2007 (5 pages).

PCT Written Opinion of the International Searching Authority for International Application No. PCT/US2007/012266, Nov. 13, 2007 (10 pages).

* cited by examiner

ANTI-OBESITY DUAL STENT

FIELD OF THE INVENTION

The present invention relates generally to anti-obesity stents and methods for using the same. More specifically, the present invention relates to anti-obesity dual stents which are secured in the duodenum adjacent to the stomach to reduce digestion and absorption of food.

BACKGROUND OF THE INVENTION

The incidence of obesity and its associated health-related problems has become significant. The causes of obesity involve a complex interplay of genetic, environmental, psycho-behavioral, endocrine, metabolic, cultural, and socio-economic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea. Obesity is a leading cause of preventable death in the U.S. The spectrum of comorbid conditions associated with obesity includes cancer, osteoarthritis, and heart disease. The economic cost of obesity is substantial.

Current treatments for obesity range from diet, exercise, behavioral modification, and pharmacotherapy to various types of surgery, with varying risks and efficacy. In general, nonsurgical treatments, although less invasive, achieve only relatively short-term and limited weight loss in most patients. Non-surgical treatments are utilized for patients such as with a body-mass index (BMI) which is greater than 30, and have not proven very effective. Surgical treatments include gastroplasty to restrict the capacity of the stomach to hold large amounts of food, such as by stapling or "gastric banding". Other surgical procedures include gastric bypass and gastric "balloons" which, when deflated, may be inserted into the stomach and then are distended by filling with saline solution.

Surgical interventions may be performed on those patients with a BMI which is greater than 40 (deemed morbidly obese). Surgical interventions may include restrictive operations that reduce the size of the stomach pouch to limit food intake. Surgical interventions may also include malabsorptive procedures that rearrange the small intestine in an attempt to decrease the functional length or efficiency of nutrient absorption, or a combination thereof. One combination procedure is Gastric Bypass (GPB or Roux-en-Y) which has been effective for most patients who maintain about 70% of excess weight loss after 5 years, and 50% thereof after 10 years. Both of these types of procedures may be performed laparoscopically, but may have complications. Also, GPB is normally irreversible. Other treatment approaches are being considered. Excess weight loss is the loss of weight which is greater than the ideal body weight.

The need exists for low cost, less invasive interventions for the treatment of obesity, including morbid obesity.

SUMMARY OF THE INVENTION

The anti-obesity dual stent of the present invention includes a tubular outer structure having outer and inner surfaces. The outer structure has proximal and distal ends. The outer structure has a lumen the outer periphery of which is defined by the inner surface of the outer structure. The outer structure is sized to fit within a duodenum in substantially coaxial relation therewith. A port structure is connected to the outer structure to provide a conduit between the outer and inner surfaces thereof.

The anti-obesity dual stent includes a tubular inner structure having outer and inner surfaces. The inner structure has proximal and distal ends. The inner structure has a lumen the outer periphery of which is defined by the inner surface of the inner structure. The inner structure is located within the lumen of the outer structure in coaxial relation therewith such that a transverse clearance is provided between the inner surface of the outer structure, and the outer surface of the inner structure.

A retainer structure is connected to the outer and inner structures. The retainer structure secures the inner structure within the duodenum such that the proximal end of the inner structure is in direct contact with a pylorus which leads to the duodenum. The proximal end of the inner structure is configured to provide communication with the pylorus such that substantially all of a chyme which exits the pylorus flows into the lumen of the inner structure. Chyme is the partially digested food which flows into the duodenum from the stomach. The lumen of the inner structure provides a conduit for the chyme therein to flow to the distal end of the inner structure. The inner structure is impervious or semi-permeable to the chyme therein.

The retainer structure further secures the outer structure within the duodenum such that the port structure receives substantially all of a digestive fluid from a papilla of Vater on an inner surface of the duodenum. The conduit of the port structure provides for the digestive fluid received therein to flow into the transverse clearance. The transverse clearance provides a conduit for the digestive fluid therein to flow to the distal ends of the outer and inner structures. The inner structure is impervious or semi-permeable to the digestive fluid in the transverse clearance within the duodenum.

Alternatively, the anti-obesity dual stent of the present invention includes a tubular papilla-supplied structure having outer and inner surfaces. The papilla-supplied structure has proximal and distal ends. The papilla-supplied structure has a lumen the outer periphery of which is defined by the inner surface of the papilla-supplied structure. A port structure is connected to the papilla-supplied structure to provide a conduit between the outer and inner surfaces thereof.

The alternative anti-obesity dual stent includes a tubular pylorus-supplied structure having outer and inner surfaces. The pylorus-supplied structure has proximal and distal ends. The pylorus-supplied structure has a lumen the outer periphery of which is defined by the inner surface of the pylorus-supplied structure.

The papilla-supplied and pylorus-supplied structures each are sized to fit longitudinally within the duodenum. The pylorus-supplied structure has a lateral orientation relative to the papilla-supplied structure.

A retainer structure is connected to the papilla-supplied and pylorus-supplied structures. The retainer structure secures the pylorus-supplied structure within the duodenum such that the chyme which exits the pylorus flows into the lumen of the pylorus-supplied structure. The lumen of the pylorus-supplied structure provides a conduit for the chyme therein to flow to the distal end of the pylorus-supplied structure. The pylorus-supplied structure is impervious or semi-permeable to the chyme therein.

The retainer structure further secures the papilla-supplied structure within the duodenum such that the port structure receives substantially all of the digestive fluid from the papilla of Vater on the inner surface of the duodenum. The conduit of the port structure provides for the digestive fluid received therein to flow into the lumen of the papilla-supplied structure which provides a conduit for the digestive fluid therein to flow to the distal end of the papilla-supplied structure. The papilla-supplied structure is impervious or semi-permeable to the digestive fluid therein.

The anti-obesity dual stent, when secured in the proper location within the duodenum, reduces or prevents mixing of the chyme and digestive fluid within the duodenum. The digestive fluid within the duodenum includes biliary and pancreatic juices which reach the interior of the duodenum by flowing through the papilla of Vater which is contiguous with the inner surface of the duodenum. The digestive fluid is supplied to the papilla of Vater by the bile and pancreatic ducts. The anti-obesity dual stent reduces or prevents mixing of the chyme and digestive fluid by reducing or preventing the digestive fluid which flows through the papilla of Vater from passing through the inner and pylorus-supplied structures. Consequently, mixing of the digestive fluid with the chyme in the region of the duodenum which is occupied by the anti-obesity dual stent is reduced or prevented. This reduces the exposure of the chyme to the digestive fluid which reduces the associated chemical breakdown thereof. This is a result of the inner and pylorus-supplied structures being semi-permeable or impervious to the chyme. The reduction in the mixing of the chyme and digestive fluid provided by the anti-obesity dual stent reduces the caloric intake by the patient. Also, this reduction in the mixing reduces the breakdown of fats because the bile is separated from the chyme over the axial length of the anti-obesity dual stent. Consequently, the chemical transformation of the chyme by the digestive fluid which is normally required for absorption of the nutrients, fats and other substances in the chyme by the duodenum is reduced.

Additionally, the anti-obesity dual stent reduces the absorption of the nutrients, fats and other substances in the chyme by the duodenum. This reduced absorption results from the inner and pylorus-supplied structures being semi-permeable or impervious to the chyme. As a result, the chyme which is contained within the inner and pylorus-supplied structures is partially or completely prevented from reaching the inner surface of the portion of the duodenum in which the anti-obesity dual stent is located. Consequently, the portion of the duodenum in which the anti-obesity dual stent is located is partially or completely prevented from absorbing the nutrients, fats and other substances in the chyme. Reducing the absorption of the nutrients, fats and other substances by the duodenum reduces the caloric intake by the patient. Also, reducing the absorption of the nutrients, fats and other substances reduces the fat intake by the patient which typically reduces the weight thereof.

The anti-obesity dual stent does not obstruct the passage and flow of the digestive fluid through the papilla of Vater. The digestive fluid includes biliary secretions which flow through the papilla of Vater. The passage and flow of the digestive fluid through the papilla of Vater is provided by the port structure and longitudinal position of the anti-obesity dual stent relative to the papilla of Vater. This allows flow of the digestive fluid through the papilla of Vater into the anti-obesity dual stent. The anti-obesity dual stent further provides for the conveyance of the digestive fluid through the stent to the distal end thereof. The passage or flow of the digestive fluid through the papilla of Vater which is not obstructed by the anti-obesity dual stent is beneficial because obstruction of such passage or flow through the papilla of Vater may be undesirable.

The anti-obesity dual stent separates the food and chyme, which flows from the stomach into the duodenum, from the digestive fluid which includes bile acids and pancreatic enzymes and which promotes lipid absorption. This separation by the anti-obesity dual stent is provided at the location thereof in the duodenum which is the beginning of the small intestine. The anti-obesity dual stent treats obesity using a mal-absorptive method. Separating the food from the digestive fluid may reduce the amount of digestion and, consequently, the amount of weight a person gains from eating a specific quantity of food.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
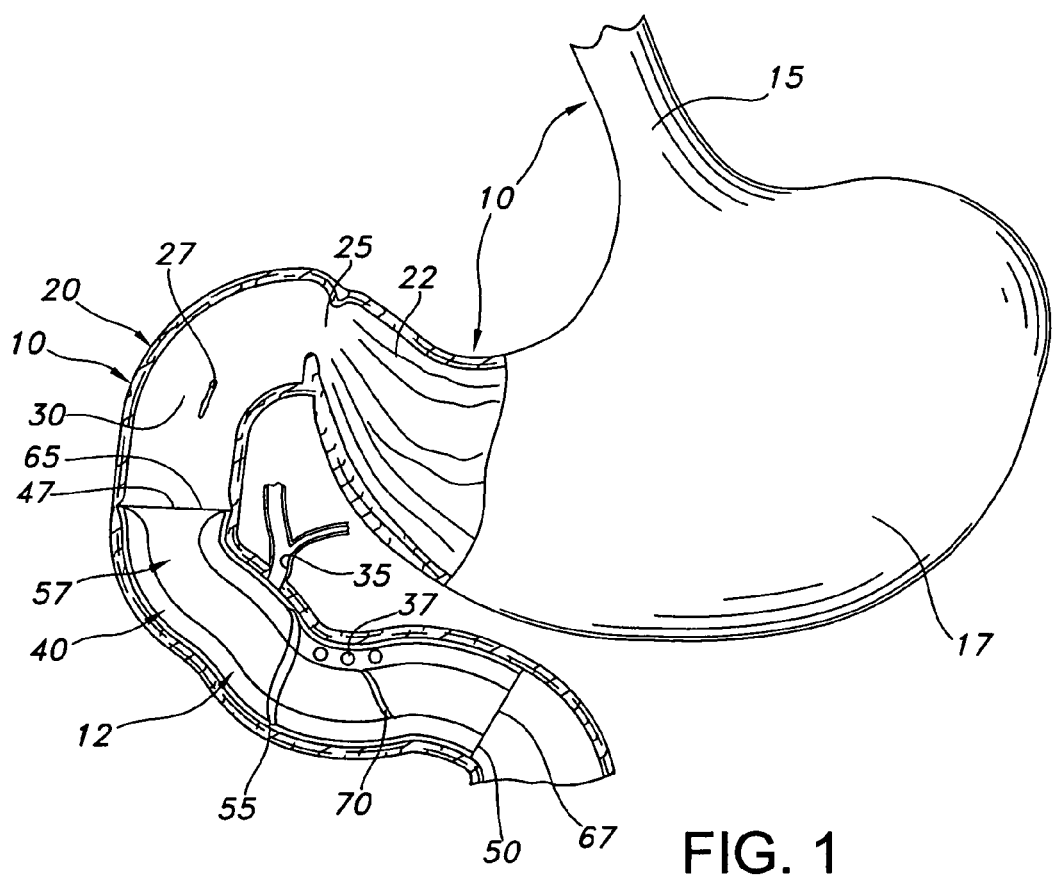
FIG. 1 is an anatomical elevational view of a stomach, duodenum and adjacent portions of the alimentary canal, the wall of the pyloric portion of the stomach and duodenum being broken away to show an anti-obesity dual stent in accordance with the present invention.

Referring to the drawings and more particularly to FIG. 1, a central portion of the alimentary canal 10 in which the anti-obesity dual stent 12 is located is illustrated. This portion of the alimentary canal 10 includes the distal segment of the esophagus 15, the stomach 17, and the duodenum 20. The duodenum 20 is the proximate segment of the small intestine. The stomach 17 has a pyloric portion 22 which leads to the duodenum 20 by way of the gastric outlet or pylorus 25. The pylorus 25 forms the distal aperture of the stomach and has an enclosing circular layer of muscle which is normally contracted to close the aperture but which relaxes to provide an open but restrictive passage. Although subject to substantial variation in different individuals, the pylorus 25 has a maximum open diameter of about 2 cm, and the duodenum 20 has a diameter which typically is about 18 to 20 mm in a representative patient. The chyme 27 passes from the pyloric portion 22 through the pylorus 25 into the duodenum 20. The duodenum 20 has an inner surface 30 and a papilla of Vater 35 which is a trumpet-mouthed dilatation of the duodenal wall at the opening of the fused bile and pancreatic ducts. The digestive fluid 37 is supplied through the papilla of Vater 35, and flows into the interior of the duodenum 20.

Figure 2:
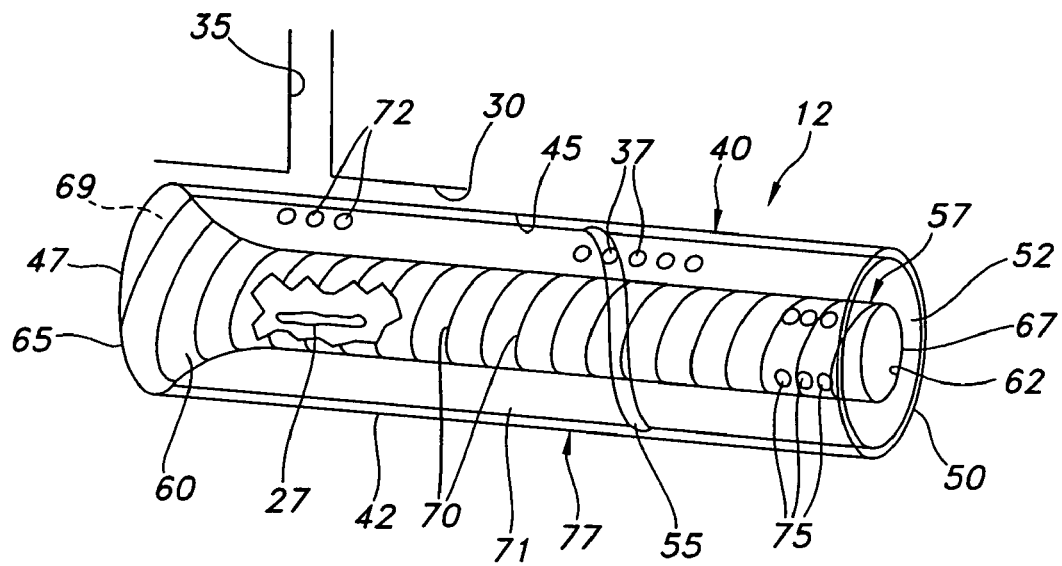
FIG. 2 is a perspective view of the anti-obesity dual stent of FIG. 1, the duodenum and papilla of Vater being shown schematically, the anti-obesity dual stent being shown as having outer and inner structures, the outer and inner structures and duodenum being illustrated as having substantially straight configurations, the outer structure being depicted as transparent to show the inner structure, the inner structure being illustrated as having a section broken away to illustrate the chyme.
Figure 3:
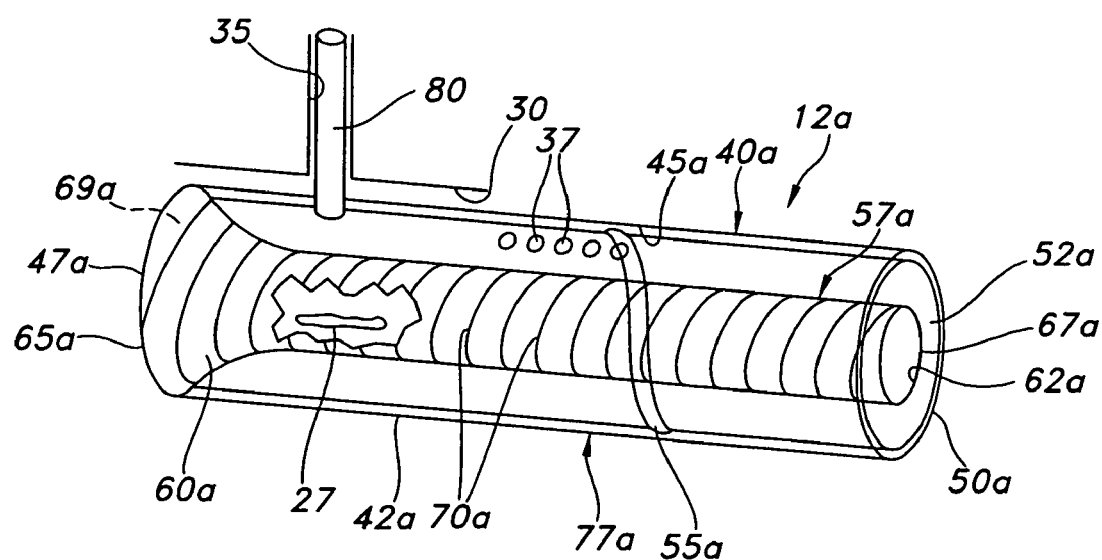
FIG. 3 is a perspective view of an alternative embodiment of the anti-obesity dual stent of FIG. 2, the duodenum and papilla of Vater being shown schematically, the anti-obesity dual stent being shown as having a side tube connected to a port structure.

The anti-obesity dual stent 12 is located within the duodenum 20 as shown in FIG. 1. The anti-obesity dual stent 12 includes a tubular outer structure 40 which has outer and inner surfaces 42, 45. The outer structure 40 has proximal and distal ends 47, 50. The outer structure 40 has a lumen 52 the outer periphery of which is defined by the inner surface 45. The anti-obesity dual stent 12 includes a groove 55 which is formed on the inner surface 45. The groove 55 has rotational and longitudinal orientations which are offset relative to the outer structure 40. These offset rotational and longitudinal orientations provide for the groove 55 to be helical where the outer structure 40 has an annular cross section. The outer structure 40 may be uncoated or coated. A port structure 72, which defines a proximal port structure, is connected to the outer structure 40. The proximal port structure 72 is adjacent to the proximal end 47 to provide a conduit between the outer and inner surfaces 42, 45. The proximal port structure 72 includes one or more orifices in the outer structure 40 such that the one or more orifices extend between the outer and inner surfaces 42, 45. The outer structure 40 is illustrated in FIGS. 1 to 3 as being transparent. Alternative embodiments of the outer structure 40 are possible which are opaque.

The anti-obesity dual stent 12 includes a tubular inner structure 57 having outer and inner surfaces 60, 62. The inner structure 57 has proximal and distal ends 65, 67. The proximal end 65 is outwardly flared. The inner structure 57 has a lumen 69 the outer periphery of which is defined by the inner surface 62. The anti-obesity dual stent 12 includes a groove 70 which is formed on the outer surface 60. The groove 70 has rotational and longitudinal orientations which are offset relative to the inner structure 57. These offset rotational and longitudinal orientations provide for the groove 70 to be helical where the inner structure 57 has an annular cross section. The inner structure 57 is coated.

The outer and inner structures 40, 57 typically have respective cross sections which are annular. Alternative embodiments of the anti-obesity dual stent 12 are possible in which the outer and inner structures 40, 57 have respective cross sections which are non-annular.

The inner structure 57 is located within the lumen 52 of the outer structure 40. The outer structure 40 has a coaxial or concentric relation to the inner structure 57. This provides a transverse clearance 71 between the inner and outer surfaces 45, 60. The transverse clearance 71 has an annular cross section where the outer and inner structures 40, 57 have respective annular cross sections. Alternative embodiments of the anti-obesity dual stent 12 are possible in which the outer structure 40 has a non-concentric relation to the inner structure 57.

A distal port structure 75 is connected to the inner structure 57. The distal port structure 75 is adjacent to the distal end 67 to provide a conduit between the transverse clearance 71 and lumen 69. The distal port structure 75 includes one or more orifices in the inner structure 57 such that the one or more orifices extend between the outer and inner surfaces 60, 62.

The outer and inner structures 40, 57 may each be formed of expanded polytetrafluoroethylene (ePTFE) or polyurethane. The outer and inner structures 40, 57 may be formed of biocompatible materials, such as polymers which may include fillers such as metals, carbon fibers, glass fibers or ceramics. Such polymers may include olefin polymers, polyethylene, polypropylene, polyvinyl chloride, polytetrafluoroethylene which is not expanded, fluorinated ethylene propylene copolymer, polyvinyl acetate, polystyrene, poly (ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the outer and inner structures 40, 57.

The outer and inner structures 40, 57 may each be a sleeve structure within which is located a respective stent structure. The sleeve structures 40, 57 may each be a PERMALUME® silicone covering for a stent structure constituted by a WALLSTENT® RX Biliary Endoprosthesis, both of which are made by the Boston Scientific Corporation.

The outer and inner structures 40, 57 may each be a stent structure, such as a WALLSTENT® RX Biliary Endoprosthesis made by the Boston Scientific Corporation. Alternatively, the stent structures may each be a NIR® Biliary Stent System made by the Boston Scientific Corporation. Further alternative stent structures are possible.

The stent structures of the outer and inner structures 40, 57 may be formed of materials such as nitinol, Elgiloy, stainless steel, cobalt chromium, including MP35N, cobalt-based alloy, tantalum, niobium, platinum, gold, titanium, combinations thereof and other biocompatible metals, polymers and materials. Additionally, the stent structures may include structural members which have an inner core formed of tantalum, gold, platinum, iridium, or a combination thereof, and an outer cladding of nitinol to provide composite members for improved radio-opacity or visibility. Examples of such composite members are disclosed in U.S. Patent Application Publication No. 2002/0035396 which is hereby incorporated by reference herein.

The stent structures of the outer and inner structures 40, 57 may have various embodiments. For example, the stent structures may be self-expanding or expandable by a balloon. The stent structures may include one or more coiled stainless steel springs, helically wound coil springs including a heat-sensitive material, or expanding stainless steel stents formed of stainless steel wire in a zig-zag pattern. The stent structures may be capable of radially contracting or expanding, such as by radial or circumferential distension or deformation. Self-expanding stent structures include stent structures which mechanically urge the stent structure to radially expand, and stent structures which expand at one or more specific temperatures as a result of the memory properties of the stent material for a specific configuration. Nitinol is a material which may be included in the stent structures for providing radial expansion thereof both by mechanical urging, or by the memory properties of the nitinol based on one or more specific temperatures. The stent structures may include one or more of the stents disclosed in U.S. Pat. Nos. 4,503,569, 4,733,665, 4,856,516, 4,580,568, 4,732,152, and 4,886,062 which are hereby incorporated by reference herein.

The outer and inner structures 40, 57 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

The outer structure 40 and the inner structure 57 therein, are sized to fit within the duodenum 20 in substantially coaxial relation therewith. The anti-obesity dual stent 12 has a retainer structure 77 connected to the outer and inner structures 40, 57. The retainer structure 77 secures the inner structure 57 within the duodenum 20 such that the proximal end 65 is in direct contact with the pylorus 25. The proximal end 65 is configured to provide communication with the pylorus 25 such that substantially all of the chyme 27 which exits the pylorus flows into the lumen 69 of the inner structure 57. The flow of substantially all of the chyme 27 from the pylorus 25 into the lumen 69 is facilitated by the outward flaring of the proximal end 65 which captures the chyme which exits the pylorus. The lumen 69 provides a conduit for the chyme 27 therein to flow to the distal end 67. The inner structure 57 is impervious or semi-permeable to the chyme 27 therein which partially or completely prevents the chyme within the inner structure from contacting the inner surface 30 of the duodenum 20 to partially or completely prevent absorption of the chyme and associated nutrients by the portion of the duodenum in which the anti-obesity dual stent 12 is located.

The retainer structure 77 further secures the outer structure 40 within the duodenum 20 such that the proximal port structure 72 receives substantially all of the digestive fluid 37 from the papilla of Vater 35. The conduit of the proximal port structure 72 provides for the digestive fluid 37 received therein to flow into the transverse clearance 71. The transverse clearance 71 provides a conduit for the digestive fluid 37 therein to flow to the distal ends 50, 67. The digestive fluid 37 in the transverse clearance 71 flows through the grooves 55, 70 in the direction toward the distal ends 50, 67. The digestive fluid 37 exits the transverse clearance 71 through the distal port structure 75. The inner structure 57 is impervious or semi-permeable to the digestive fluid 37 in the transverse clearance 71 within the duodenum 20.

The flow of the digestive fluid 37 through the grooves 55, 70 results in an increase in the distance over which the digestive fluid flows to the distal port structure 75. This increases the duration of the flow of the digestive fluid 37 through the transverse clearance 71 from the proximal to distal port structures 72, 75. Consequently, the chyme 27 within the inner structure 57 typically exits therefrom through the distal end 67 before the exit of the digestive fluid 37 through the distal port structure 75. The delay in the exit of the digestive fluid 37 through the distal port structure 75 results from the flow of the chyme 27 into the duodenum 20 and the substantially simultaneous supply of the digestive fluid 37 to the transverse clearance 71, and the increased duration of the flow of the digestive fluid through the transverse clearance relative to the duration of the flow of the chyme 27 through the lumen 69. The delayed exit of the digestive fluid 37 through the distal port structure 75 relative to the exit of the chyme 27 through the distal end 67 reduces the mixing of the digestive fluid and chyme since substantially all or at least a portion of the chyme is downstream of the digestive fluid within the duodenum 20. The digestive fluid 37 which enters the duodenum 20 without mixing with the chyme 27 may be absorbed by the inner surface 30 of the duodenum 20. This reduces the mixing of the digestive fluid 37 and chyme 27 which reduces the digestion thereof and absorption of the chyme and associated nutrients by the inner surface 30.

The retainer structure 77 is the transverse dimension of the outer surface 42 of the outer structure 40 being sufficiently large to press against the inner surface 30 of the duodenum 20 when the proximal port structure 72 has substantially the same longitudinal position as the papilla of Vater 35. The pressing of the outer surface 42 against the inner surface 30 provides resistance to longitudinal displacement of the outer structure 40 relative to the duodenum 20. The transverse dimension of the outer surface 42 corresponds to the diameter thereof where the outer structure 40 has an annular cross section. Alternatively, the retainer structure 77 may include a semi-rigid band which is attached to the outer structure 40. Such a semi-rigid band may be ratcheted open to an outer transverse dimension which is sufficient to engage the inner surface 30 to provide resistance to longitudinal displacement of the outer structure 40 relative to the duodenum 20. Such a semi-rigid band may include metal or polymeric material.

A further alternative embodiment of the retainer structure 77 includes sutures for securing the outer structure 40 to the inner surface 30 to prevent migration and rotation of the outer structure relative to the duodenum 20. An additional alternative embodiment of the retainer structure 77 includes sutures for securing the outer structure 40 to the stomach 17. A further alternative embodiment of the retainer structure 77 includes the outward flaring of the proximal ends 47, 65 and distal ends 60, 67. Such outward flaring provides for the outer and inner structures 40, 57 to fit snugly within the duodenum 20 and possible other locations of deployment.

An alternative embodiment of the anti-obesity dual stent 12a is shown in FIG. 3. Parts illustrated in FIG. 3 which correspond to parts illustrated in FIGS. 1 and 2 have, in FIG. 3, the same reference numeral as in FIGS. 1 and 2 with the addition of the suffix "a". In this alternative embodiment, the anti-obesity dual stent 12a includes a side tube 80 which is connected to the proximal port structure 72a and communicates with the transverse clearance 71a. The side tube 80 is insertable through the papilla of Vater 35 such that the digestive fluid 37 therein is conveyed through the side tube into the transverse clearance 71a. The side tube 80 resists longitudinal and rotational displacement of the outer structure 40a relative to the duodenum 20 when the side tube is inserted into the papilla of Vater 35. The resistance provided by the side tube 80 prevents migration of the outer structure 40a within the duodenum 20.

Figure 4:
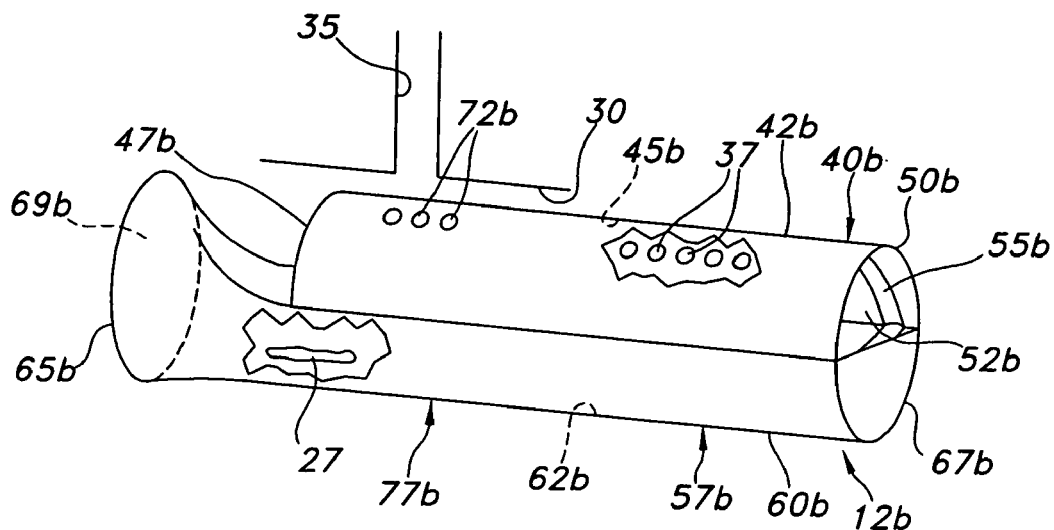
FIG. 4 is a perspective view of an alternative embodiment of the anti-obesity dual stent of FIG. 1, the duodenum and papilla of Vater being shown schematically, the anti-obesity dual stent being shown as having a papilla-supplied structure which has a lateral orientation relative to a pylorus-supplied structure, the papilla-supplied and pyloryus-supplied structures and duodenum being illustrated as having substantially straight configurations, the papilla-supplied and pylorus-supplied structures being shown as having sections broken away to illustrate the digestive fluid and chyme, respectively.

An alternative embodiment of the anti-obesity dual stent 12b is shown in FIG. 4. Parts illustrated in FIG. 4 which correspond to parts illustrated in FIGS. 1 and 2 have, in FIG. 4, the same reference numeral as in FIGS. 1 and 2 with the addition of the suffix "b". In this alternative embodiment, the anti-obesity dual stent 12b includes a tubular papilla-supplied structure 40b which has outer and inner surfaces 42b, 45b. The papilla-supplied structure 40b has proximal and distal ends 47b, 50b. The papilla-supplied structure 40b has a lumen 52b the outer periphery of which is defined by the inner surface 45b. The anti-obesity dual stent 12b includes a groove 55b which is formed on the inner surface 45b. The groove 55b has rotational and longitudinal orientations which are offset relative to the papilla-supplied structure 40b. These offset rotational and longitudinal orientations provide for the groove 55b to be helical where the papilla-supplied structure 40b has an annular cross section. The papilla-supplied structure 40b is uncoated.

A proximal port structure 72b is connected to the papilla-supplied structure 40b. The proximal port structure 72b is adjacent to the proximal end 47b to provide a conduit between the outer and inner surfaces 42b, 45b. The proximal port structure 72b includes one or more orifices in the papilla-supplied structure 40b such that the one or more orifices extend between the outer and inner surfaces 42b, 45b.

The anti-obesity dual stent 12b includes a tubular pylorus-supplied structure 57b having outer and inner surfaces 60b, 62b. The pylorus-supplied structure 57b has proximal and distal ends 65b, 67b. The proximal end 65b is outwardly flared. The pylorus-supplied structure 57b has a lumen 69b the outer periphery of which is defined by the inner surface 62b. The inner structure 57 is coated.

The papilla-supplied and pylorus-supplied structures 40b, 57b typically have respective cross sections which are annular. Alternative embodiments of the anti-obesity dual stent 12b are possible in which the papilla-supplied and pylorus-supplied structures 40b, 57b have respective cross sections which are non-annular.

The papilla-supplied and pylorus-supplied structures 40b, 57b are sized to fit longitudinally within the duodenum 20. The pylorus-supplied structure 57b has a lateral orientation relative to the papilla-supplied structure 40b.

The anti-obesity dual stent 12b has a retainer structure 77b connected to the papilla-supplied and pylorus-supplied structures 40b, 57b. The retainer structure 77b secures the pylorus-supplied structure 57b within the duodenum 20 such that the proximal end 65b is in direct contact with the pylorus 25. The proximal end 65b is configured to provide communication with the pylorus 25 such that substantially all of the chyme 27 which exits the pylorus flows into the lumen 69b of the pylorus-supplied structure 57b. The flow of substantially all of the chyme 27 from the pylorus 25 into the lumen 69b is facilitated by the outward flaring of the proximal end 65b. The lumen 69b provides a conduit for the chyme 27 therein to flow to the distal end 67b. The pylorus-supplied structure 57b is impervious or semi-permeable to the chyme 27 therein which partially or completely prevents the chyme within the pylorus-supplied structure from contacting the inner surface 30 of the duodenum 20 to partially or completely prevent absorption of the chyme and associated nutrients by the portion of the duodenum in which the anti-obesity dual stent 12b is located.

The retainer structure 77b further secures the papilla-supplied structure 40b within the duodenum 20 such that the proximal port structure 72b receives substantially all of the digestive fluid 37 from the papilla of Vater 35. The conduit of the proximal port structure 72b provides for the digestive fluid 37 received therein to flow into the lumen 52b. The lumen 52b provides a conduit for the digestive fluid 37 therein to flow to the distal end 50b. The digestive fluid 37 in the lumen 52b flows through the groove 55b in the direction toward the distal end 50b. The digestive fluid 37 exits the lumen 52b through the distal end 50b. The papilla-supplied structure 57b is impervious or semi-permeable to the digestive fluid 37 in the lumen 52b within the duodenum 20.

The flow of the digestive fluid 37 through the groove 55b results in an increase in the distance over which the digestive fluid flows to the distal end 50b. This increases the duration of the flow of the digestive fluid 37 through the lumen 52b from the proximal port structure 72b to the distal end 50b. Consequently, the chyme 27 within the pylorus-supplied structure 57b typically exits therefrom through the distal end 67b before the exit of the digestive fluid 37 through the distal end 50b. The delay in the exit of the digestive fluid 37 through the distal end 50b results from the flow of the chyme 27 into the duodenum 20 and the substantially simultaneous supply of the digestive fluid 37 to the lumen 52b, and the increased duration of the flow of the digestive fluid through the lumen 52b relative to the duration of the flow of the chyme 27 through the lumen 69b. The delayed exit of the digestive fluid 37 through the distal end 50b relative to the exit of the chyme 27 through the distal end 67b reduces the mixing of the digestive fluid and chyme since substantially all or at least a portion of the chyme is downstream of the digestive fluid within the duodenum 20. The digestive fluid 37 which enters the duodenum 20 without mixing with the chyme 27 may be absorbed by the inner surface 30 of the duodenum 20. This reduces the mixing of the digestive fluid 37 and chyme 27 which reduces the digestion thereof and absorption of the chyme and associated nutrients by the inner surface 30.

The retainer structure 77b is the transverse dimension of the outer surfaces 42b, 60b of the papilla-supplied and pylorus-supplied structures 40b, 57b being sufficiently large to press against the inner surface 30 of the duodenum 20 when the proximal port structure 72b has substantially the same longitudinal position as the papilla of Vater 35. The pressing of the outer surfaces 42b, 60b against the inner surface 30 provides resistance to longitudinal displacement of the papilla-supplied and pylorus-supplied structures 40b, 57b relative to the duodenum 20. The transverse dimensions of the outer surfaces 42b, 60b correspond to the respective diameters thereof where the papilla-supplied and pylorus-supplied structures 40b, 57b have respective annular cross sections. Alternatively, the retainer structure 77b may include a semi-rigid band which is attached to the papilla-supplied and pylorus-supplied structures 40b, 57b. Such a semi-rigid band may be ratcheted open to an outer transverse dimension which is sufficient to engage the inner surface 30 to provide resistance to longitudinal displacement of the papilla-supplied and pylorus-supplied structures 40b, 57b relative to the duodenum 20. Such a semi-rigid band may include metal or polymeric material.

A further alternative embodiment of the retainer structure 77b includes sutures for securing the papilla-supplied and pylorus-supplied structures 40b, 57b to the inner surface 30 to prevent migration and rotation of the papilla-supplied and pylorus-supplied structures relative to the duodenum 20. An additional alternative embodiment of the retainer structure 77b includes sutures for securing the papilla-supplied and pylorus-supplied structures 40b, 57b to the stomach 17. A further alternative embodiment of the retainer structure 77b includes the outward flaring of the proximal ends 47b, 65b and distal ends 60b, 67b. Such outward flaring provides for the papilla-supplied and pylorus-supplied structures 40b, 57b to fit snugly within the duodenum 20 and possible other locations of deployment.

Figure 5:
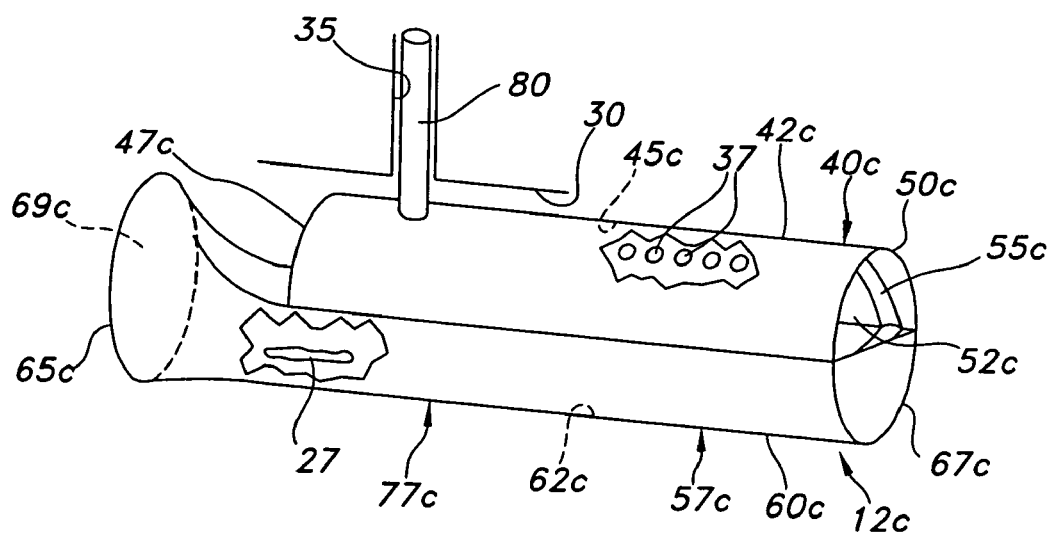
FIG. 5 is a perspective view of an alternative embodiment of the anti-obesity dual stent of FIG. 4, the duodenum and papilla of the Vater being shown schematically, the anti-obesity dual stent being shown as having a side tube connected to a port structure.

An alternative embodiment of the anti-obesity dual stent 12c is shown in FIG. 5. Parts illustrated in FIG. 5 which correspond to parts illustrated in FIGS. 1 and 2 have, in FIG. 5, the same reference numeral as in FIGS. 1 and 2 with the addition of the suffix "c". In this alternative embodiment, the anti-obesity dual stent 12c includes a side tube 82 which is connected to the proximal port structure 72c and communicates with the lumen 52c. The side tube 82 is insertable through the papilla of Vater 35 such that the digestive fluid 37 therein is conveyed through the side tube into the lumen 52c. The side tube 82 resists longitudinal and rotational displacement of the papilla-supplied structure 40c relative to the duodenum 20 when the side tube is inserted into the papilla of Vater 35. The resistance provided by the side tube 82 prevents migration of the papilla-supplied structure 40c within the duodenum 20.

An anti-obesity stent, such as the anti-obesity stent 12, may be used according to a method for inducing weight loss in a patient. The method includes inserting tubular outer and inner structures of the anti-obesity dual stent into a duodenum, such as the duodenum 20, in substantially coaxial relation therewith. Embodiments of the outer and inner structures to which this inserting may be applied include the outer and inner structures 40, 57. The outer and inner structures have respective outer and inner surfaces and proximal and distal ends, and respective lumens. The lumen of the outer structure has an outer periphery which is defined by the inner surface of the outer structure. The inner structure is located within the lumen of the outer structure in coaxial relation therewith such that a transverse clearance is provided between the inner surface of the outer structure and the outer surface of the inner structure. The lumen of the inner structure has an outer periphery which is defined by the inner surface of the inner structure. The anti-obesity dual stent has a port structure connected to the outer structure to provide a conduit between the outer and inner surfaces thereof.

The method further includes locating the outer and inner structures within and longitudinally relative to the duodenum such that the proximal ends of the outer and inner structures have corresponding proximal positions relative to a papilla of Vater, such as the papilla of Vater 35. Embodiments of the proximal ends of the outer and inner structures which may be positioned according to this locating include the proximal ends 47, 65.

The locating further positions the anti-obesity dual stent such that the distal ends of the outer and inner structures have corresponding distal positions relative to the papilla of Vater. Embodiments of the distal ends of the outer and inner structures which may be positioned according to this locating include the distal ends 50, 67.

The locating further positions the anti-obesity dual stent such that the port structure is positioned to receive the digestive fluid from the papilla of Vater. An embodiment of the port structure which may be positioned by this locating is the proximal port structure 72. The conduit of the port structure provides for the digestive fluid, such as the digestive fluid 37, received therein to flow into the transverse clearance between the inner surface of the outer structure and the outer surface of the inner structure. An embodiment of the transverse clearance into which the digestive fluid may flow is the transverse clearance 71.

The locating further positions the anti-obesity dual stent such that the lumen of the inner structure communicates through the proximal end thereof with the pylorus, such as the pylorus 25. An embodiment of the proximal end which may be positioned by this locating is the proximal end 65. An embodiment of the lumen which communicates with the pylorus is the lumen 69.

The method further includes engaging a retainer structure of the anti-obesity dual stent with the inner surface of the duodenum, such as the inner surface 30. This engaging secures the port structure in the position thereof to receive the digestive fluid from the papilla of Vater. An embodiment of the retainer structure to which this engaging may be applied is the retainer structure 77. The engaging further secures the inner structure in the position thereof to provide the communication between the lumen of the inner structure and pylorus through the proximal end of the inner structure.

An anti-obesity dual stent, such as the anti-obesity dual stent 12b, may be used according to a method for inducing weight loss in a patient. The method includes inserting tubular papilla-supplied and pylorus-supplied structures of the anti-obesity dual stent into a duodenum, such as the duodenum 20, in substantially coaxial relation therewith. Embodiments of the papilla-supplied and pylorus-supplied structures to which this inserting may be applied include the papilla-supplied and pylorus-supplied structures 40b, 57b. The papilla-supplied and pylorus-supplied structures have respective outer and inner surfaces and proximal and distal ends, and respective lumens. The lumen of the pylorus-supplied structure has an outer periphery which is defined by the inner surface of the pylorus-supplied structure. The lumen of the papilla-supplied structure has an outer periphery which is defined by the inner surface of the papilla-supplied structure. The pylorus-supplied structure has a lateral orientation relative to the papilla-supplied structure. The anti-obesity dual stent has a port structure connected to the papilla-supplied structure to provide a conduit between the outer and inner surfaces thereof.

The method further includes locating the papilla-supplied and pylorus-supplied structures within and longitudinally relative to the duodenum such that the proximal ends of the papilla-supplied and pylorus-supplied structures have corresponding proximal positions relative to a papilla of Vater, such as the papilla of Vater 35. Embodiments of the proximal ends of the papilla-supplied and pylorus-supplied structures which may be positioned according to this locating include the distal ends 47b, 65b.

The locating further positions the anti-obesity dual stent such that the distal ends of the papilla-supplied and pylorus-supplied structures have corresponding distal positions relative to the papilla of Vater. Embodiments of the distal ends of the papilla-supplied and pylorus-supplied structures which may be positioned according to this locating include the distal ends 50b, 67b.

The locating further positions the anti-obesity dual stent such that the port structure is positioned to receive the digestive fluid from the papilla of Vater. An embodiment of the port structure which may be positioned by this locating is the proximal port structure 72b. The conduit of the port structure provides for the digestive fluid, such as the digestive fluid 37, received therein to flow into the lumen of the papilla-supplied structure. An embodiment of the lumen into which the digestive fluid may flow is the lumen 52b.

The locating further positions the anti-obesity dual stent such that the lumen of the pylorus-supplied structure communicates through the proximal end thereof with the pylorus, such as the pylorus 25. An embodiment of the proximal end which may be positioned by this locating is the proximal end 65b. An embodiment of the lumen which communicates with the pylorus is the lumen 69b.

The method further includes engaging a retainer structure of the anti-obesity dual stent with the inner surface of the duodenum, such as the inner surface 30. This engaging secures the port structure in the position thereof to receive the digestive fluid from the papilla of Vater. An embodiment of the retainer structure to which this engaging may be applied is the retainer structure 77b. The engaging further secures the pylorus-supplied structure in the position thereof to provide the communication between the lumen of the pylorus-supplied structure and pylorus through the proximal end of the pylorus-supplied structure.

U.S. Pat. No. 6,740,121 is hereby incorporated by reference herein. The following U.S. patent applications are hereby incorporated by reference herein:

Title: Anti-Obesity Stent; Inventors: Barry Weitzner, Taryn Deneault, Katie Krueger, Claude Clerc, Harold W. Martins, and William Bertolino; Filed on same date as present U.S. patent application Ser. No. 11/443,537;

Title: Anti-Obesity Diverter Structure; Inventors: Katie Krueger, and Harold W. Martins; Filed on same date as present U.S. patent application Ser. No. 11/443,516; and Title: Anti-Obesity Flow Controller; Inventor: Barry Weitzner; Filed on same date as present U.S. patent application Ser. No. 11/443,544.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A dual stent comprising:
a tubular outer structure having outer and inner surfaces, said outer structure having proximal and distal ends,
said outer structure having a lumen which has an outer periphery defined by said inner surface of said outer structure,
a port structure connected to said outer structure,
a tubular inner structure having outer and inner surfaces, said inner structure having proximal and distal ends,
said inner structure having a lumen which has an outer periphery defined by said inner surface of said inner structure,
said inner structure being located within said lumen of the outer structure in coaxial relation therewith such that a transverse clearance is provided between the inner surface of the outer structure and the outer surface of the inner structure, wherein
a retainer structure is connected to said outer and inner structures, said inner structure being impervious or semi-permeable to chyme, and
said inner structure being impervious or semi-permeable to digestive fluid;
wherein the inner and outer structures are each a sleeve structure within which is located a stent structure;
wherein a groove is formed on the outer surface of the inner structure, said groove having rotational and longitudinal orientations which are offset relative to the inner structure, and
wherein a groove is formed on the inner surface of the outer structure, said groove having rotational and longitudinal orientations which are offset relative to the outer structure.

2. A dual stent according to claim 1, wherein said proximal end of said inner structure is outwardly flared.

3. A dual stent according to claim 1, wherein said inner structure is coated and said outer structure is uncoated.

4. A dual stent according to claim 1, wherein said port structure comprises one or more orifices in said outer structure such that said one or more orifices extend between said outer and inner surfaces of said outer structure.

5. A dual stent according to claim 1, wherein said port structure defines a proximal port structure, and wherein
said dual stent further comprises a distal port structure connected to said inner structure, said distal port structure being adjacent to said distal end of said inner structure to provide a conduit between said lumen of said inner structure and said transverse clearance.

6. A dual stent according to claim 5, wherein said distal port structure comprises one or more orifices in said inner structure such that said one or more orifices extend between said outer and inner surfaces of said inner structure.

7. A dual stent according to claim 1, and further comprising a side tube which is connected to said port structure and communicates with said transverse clearance, said side tube being insertable into the papilla of Vater such that the digestive fluid therein is conveyed through said side tube into said lumen of said transverse clearance, said side tube resisting longitudinal and rotational displacement of said outer structure relative to the duodenum when said side tube is inserted into the papilla of Vater.

8. A dual stent of claim 1,
wherein the tubular outer structure and tubular inner structure are formed of a material selected from the group consisting of expanded polytetrafluoroethylene, olefin polymers, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, polyurethane, polyurea, silicone rubbers, polyamides, polycarbonates, polyaldehydes, natural rubbers, polyester copolymers, styrene-butadiene copolymers, polyethers, polyesters, polypropylenes, polyethylenes, polyurethanes, polyolefins, polyvinyls, polymethylacetates, polyamides, naphthalane dicarboxylene derivatives, and natural silk.

9. The dual stent of claim 8, wherein the tubular outer structure comprises expanded polytetrafluoroethylene.

10. The dual stent of claim 8, wherein the tubular inner structure comprises expanded polytetrafluoroethylene.

11. A dual stent of claim 1,
wherein the retainer structure comprises a semi-rigid band.

12. A method for inducing weight loss in a patient, said method comprising:
inserting tubular outer and inner structures of an anti-obesity dual stent into a duodenum in substantially coaxial relation therewith, the outer and inner structures having respective outer and inner surfaces and proximal and distal ends, the outer and inner structures having respective lumens, the lumen of the outer structure having an outer periphery which is defined by the inner surface of the outer structure, the inner structure being located within the lumen of the outer structure in coaxial relation therewith such that a transverse clearance is provided between the inner surface of the outer structure and the outer surface of the inner structure, the lumen of the inner structure having an outer periphery which is defined by the inner surface of the inner structure, the anti-obesity dual stent having a port structure connected to said outer structure to provide a conduit between said outer and inner surfaces thereof;

locating the outer and inner structures within and longitudinally relative to the duodenum such that the proximal ends of the outer and inner structures have corresponding proximal positions relative to a papilla of Vater on an inner surface of the duodenum, said locating further positioning the distal ends of the outer and inner structures to have corresponding distal positions relative to the papilla of Vater, said locating further positioning the port structure to receive a digestive fluid from the papilla of Vater, the conduit of the port structure providing for the digestive fluid received therein to flow into the transverse clearance, said locating further positioning the lumen of the inner structure to communicate through the proximal end thereof with a pylorus which leads to the duodenum; and engaging a retainer structure of the anti-obesity dual stent with the inner surface of the duodenum to secure the port structure in the position thereof to receive the digestive fluid from the papilla of Vater, wherein said engaging further comprises securing the inner structure in the position thereof to provide the communication through the proximal end of the inner structure between the lumen thereof and pylorus; and wherein the inner and outer structures are each a sleeve structure within which is located a stent structure;

wherein a groove is formed on the outer surface of the inner structure, said groove having rotational and longitudinal orientations which are offset relative to the inner structure, and wherein a groove is formed on the inner surface of the outer structure, said groove having rotational and longitudinal orientations which are offset relative to the outer structure.

* * * * *